United States Patent
Barreca et al.

(12)

(10) Patent No.: US 6,355,836 B1
(45) Date of Patent: Mar. 12, 2002

(54) PROCESS FOR THE PREPARATION OF CIS 5-FLUORO-2-METHYL-1[P-(METHYLTHIO) BENZYLIDEN]-INDEN-3-ACETIC ACID

(75) Inventors: Giuseppe Barreca, Montevecchia; Vincenzo Cannata, Sasso Marconi, both of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/677,842

(22) Filed: Oct. 3, 2000

(30) Foreign Application Priority Data

Oct. 4, 1999 (IT) .......................... MI99A2061

(51) Int. Cl.[7] .......................................... C07C 315/00
(52) U.S. Cl. ........................................ 562/428; 562/429
(58) Field of Search .................. 562/428, 429

(56) References Cited

U.S. PATENT DOCUMENTS 3,654,349 A    4/1972  Shen et al. ................. 260/515
3,692,651 A  *  9/1972  Meyer et al.
4,748,271 A  *  5/1988  Meneghin et al.

FOREIGN PATENT DOCUMENTS

CA          940144      *  1/1974
EP       0 206 241 A1     12/1986

OTHER PUBLICATIONS

The Merck Index, Twefth Edition, p. 1536, No. 9155 (1996).

* cited by examiner

Primary Examiner—Gary Geist
Assistant Examiner—Hector M Reyes
(74) Attorney, Agent, or Firm—Arent Fox Kintner Plotkin Kahn

(57) ABSTRACT

An isomerization process of trans-5-fluoro-2-methyl-1-[p-(methylthio)benzyliden]inden-3-acetic acid for the treatment of sodium salt in methanol and in the presence of a base at 70±2° C. is described.

4 Claims, No Drawings

PROCESS FOR THE PREPARATION OF CIS 5-FLUORO-2-METHYL-1[P-(METHYLTHIO) BENZYLIDEN]-INDEN-3-ACETIC ACID

The present invention relates to a process for the preparation of cis 5-fluoro-2-methyl-1-[p-(methylthio) benzyliden]inden-3-acetic acid and, more particularly, it relates to a process for the isomerization of trans-5-fluoro-2-methyl-1-[p-(methylthio)benzyliden]inden-3-acetic acid into the corresponding cis isomer, an intermediate useful for the synthesis of sulindac.

Sulindac, cis 5-fluoro-2-methyl-1-[p-(methylsulphinyl) benzyliden]inden-3-acetic acid, a known anti-inflammatory drug (The Merck Index XII ed., page 1536, no. 9155) is generally prepared according to the synthetic scheme herein below reported, as described in the U.S. Pat. No. 3,654,349 (Merck).

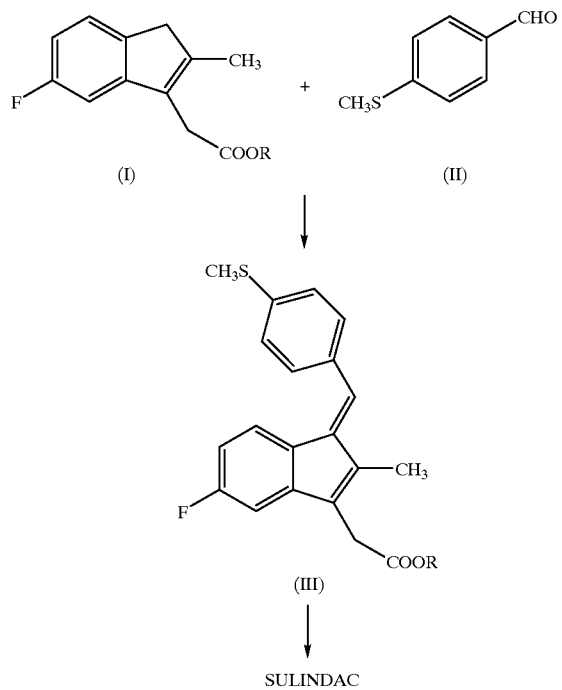

wherein R is hydrogen or a $C_1$–$C_6$ alkyl.

The condensation between 5-fluoro-2-methyl-inden-3-acetic acid (or an ester thereof) and p-methylthiobenzaldehyde is carried out in methanol, in the presence of sodium methoxide.

The drawback of the condensation described in U.S. Pat. No. 3,654,349 is that the intermediate III-cis is obtained in admixture with remarkable amounts (>10%) of the III-trans isomer, so making necessary an isomerization reaction as described, for example, in the U.S. Pat. No. 3,692,651 (Merck).

The isomerization is carried out on a mixture of sulindac (cis isomer) and of its trans isomer or on trans-sulindac by treating with iodine or by irradiating with ultra violet light.

A method for carrying out the condensation reaction without the formation of the III-trans isomer is described in the European patent application no. 0 206 241 (Zambon). We have now found a method for the isomerization of trans 5-fluoro-2-methyl-1-[p-(methylthio)benzyliden]inden-3-acetic acid.

Therefore, object of the present invention is an isomerization process of trans 5-fluoro-2-methyl-1-[p-(methylthio) benzyliden]inden-3-acetic acid consisting in treating the sodium salt of trans 5-fluoro-2-methyl-1-[p-(methylthio) benzyliden]inden-3-acetic acid in methanol and in the presence of a base at the temperature of 70±2° C.

Examples of bases, which can be used in the present process, are alkali or alkaline-earth hydroxides or $C_1$–$C_4$ alkoxides, preferably sodium hydroxide or $C_1$–$C_4$ alkoxides.

Still more preferably sodium methoxide is used.

Under the conditions of the process object of the present invention, the isomerization of trans 5-fluoro-2-methyl-1-[p-(methylthio)benzyliden]inden-3-acetic acid to cis 5-fluoro-2-methyl-1-[p-(methylthio)benzyliden]inden-3-acetic acid and the contemporaneous precipitation of the cis isomer are observed.

In such a way, the cis isomer comes out of the reaction equilibrium and the isomerization goes on up to a practically complete conversion.

The process object of the present invention can be used for the isomerization of trans 5-fluoro-2-methyl-1-[p-(methylthio)benzyliden]inden-3-acetic acid or of cis-trans mixtures of 5-fluoro-2-methyl-1-[p-(methylthio)benzyliden] inden-3-acetic acid prepared by one of the synthetic methods described in the literature.

The working conditions of the present process allow also the isomerization of the exo somer of the compound of formula III, when it is present in the mixture to be isomerized.

In a preferred embodiment, the process object of the present invention is used to obtain cis 5-fluoro-2-methyl-1-[p-(methylthio)benzyliden]inden-3-acetic acid directly from the reaction mixture of 5-fluoro-2-methyl-inden-3-acetic acid with p-methylthiobenzaldehyde in methanol and sodium methoxide.

In this way, at the end of the condensation reaction, the reaction mixture is heated at 70±2° C. for some hours and then cooled at a room temperature, directly obtaining cis 5-fluoro-2-methyl-1-[p-(methylthio)benzyliden]inden-3-acetic acid with a content of trans isomer lower than 0.5%, suitable for the preparation of sulindac.

In order to better illustrate the present invention, the following examples are now given.

EXAMPLE 1

In a 1.5 l double-jacket reactor, equipped with mechanic stirrer, thermometer and condenser, kept under nitrogen, 5-fluoro-2-methyl-inden-3-acetic acid (103.1 g; 0.50 moles), methanol (85 ml) and a 30% sodium methoxide solution (198.0 g; 1.10 moles) were charged. The suspension was heated to the reflux temperature (about 70° C.) and p-methylthiobenzaldehyde (80.6 g; 0.53 moles) was added dropwise. The solution was kept under these conditions for about 3 hours and the end of the reaction (starting compound lower than 2%) was checked by quantitative TLC (eluent hexane:ethyl acetate:acetic acid=50:45:5).

In the reaction mixture the isomer ratio was cis:trans:exo= 84:14:2.

The solution was cooled with external water up to the formation of a very thick solid mass. The mixture was brought again to the temperature of 70° C., kept under these conditions for about 1 hour (ratio cis:trans:exo=95:3:2) and then cooled in about 4 hours at 15–20° C. After keeping the reaction mixture under stirring at 15–20° C. for 2 hours (ratio cis:trans:exo=95:3:2), acetic acid (72.0 g) was added dropwise in about 1 hour, keeping the temperature below 30° C. Then water (350.0 ml) was added, the mixture (volume=1000 ml) was heated at 45–50° C. and, by application of light vacuum, the solvent was distilled off up to reach a final volume of about 650 ml. Ethyl acetate (350 ml) was added to the resultant mixture and the mass was heated at the reflux temperature (71° C.). After 1 hour under these conditions, the mixture was cooled in about 4 hours at 15–20° C. After filtration, the solid was washed with water (2×50 ml) and with ethyl acetate (3×50 ml). 167 g of wet product were obtained. After drying under vacuum at 70° C. for 18 hours, 145 g of 5-fluoro-2-methyl-1-[p-(methylthio)benzyliden]inden-3-acetic acid were obtained (85.3% yield—cis:trans ratio $\geq$99.7).

The mother liquors were added to the washings, the organic phase was separated and the organic phase washed with water (200.0 ml). The organic solution was concentrated at 40–50° C. up to obtain a residual volume of about 100.0 ml, cooled at 15–20° C. in 3 hours and filtered. The solid was washed with ethyl acetate (3×10 ml) obtaining 11.2 g of wet product which, after drying under vacuum at 70° C., gave further 10.0 g of 5-fluoro-2-methyl-1-[p-(methylthio)benzyliden]inden-3-acetic acid (5.9% yield—cis:trans ratio $\geq$99.7).

Total yield 91.2%.

EXAMPLE 2

The mother liquors from crystallization obtained as described in example 1 were concentrated to residue (2.0 g) and titred by $^1$H-NMR (solvent: DMSO) by using tert-butanol as internal standard. The so calculated isomer ratio was cis:trans:exo=34.1:34.6:31.3 with a 70% titre.

The residue was charged in a 50 ml double-jacket reactor, equipped with mechanic stirrer, thermometer and refrigerator, kept under nitrogen, together with methanol (20.0 ml) and a 30% w/w sodium methoxide solution (4.0 g). The solution was heated under reflux, kept under these conditions overnight and poured into 2N hydrochloric acid (100.0 ml).

The mixture was extracted with methylene chloride (100.0 ml), the phases were separated and the organic phase was washed with water (100.0 ml). By concentration up to residue under reduced pressure 2.05 g of a solid which, titred by $^1$H-NMR as above described, resulted to be a mixture cis:trans:exo in a ratio 76.2:12.7:11.1 with a total titre of 68.5%.

What we claims is:

1. An isomerization process of trans 5-fluoro-2-methyl-1-[p-(methylthio)benzyliden]inden-3-acetic acid consisting in treating the sodium salt of trans 5-fluoro-2-methyl-1-[p-(methylthio)benzyliden]inden-3-acetic acid in methanol and in the presence of a base at a temperature of 70±2° C.

2. A process according to claim 1 wherein the base is selected among sodium hydroxide and sodium $C_1$–$C_4$ alkoxides.

3. A process according to claim 1 wherein the base is sodium methoxide.

4. A process for the preparation of cis 5-fluoro-2-methyl-1-[p-(methylthio)benzyliden]inden-3-acetic acid which comprises an isomerization process according to claim 1.

* * * * *